United States Patent [19]

Spescha et al.

[11] 4,058,962
[45] Nov. 22, 1977

[54] METHOD AND APPARATUS FOR DETECTING PERIODIC YARN IRREGULARITIES IN A YARN BETWEEN A YARN FORMING STAGE AND A YARN WINDING STAGE

[75] Inventors: Gelli Spescha; André Lattion, both of Winterthur, Switzerland

[73] Assignee: Rieter Machine Works, Ltd., Winterthur, Switzerland

[21] Appl. No.: 760,575

[22] Filed: Jan. 19, 1977

[30] Foreign Application Priority Data

Jan. 26, 1976 Switzerland .......................... 888/76

[51] Int. Cl.$^2$ ............................................ D01H 13/22
[52] U.S. Cl. ..................................... 57/34 R; 28/227; 57/156; 73/160
[58] Field of Search .................. 57/34 R, 81, 156; 324/61 R, 71 R; 19/.2–.26; 73/160; 28/64; 226/45; 242/36, 49; 340/259

[56] References Cited

U.S. PATENT DOCUMENTS

| | | | |
|---|---|---|---|
| 2,641,960 | 6/1953 | Strother | 73/160 X |
| 3,069,621 | 12/1962 | Buthcaz et al. | 324/61 R |
| 3,303,698 | 2/1967 | Loepfe | 73/160 |
| 4,007,457 | 2/1977 | Aeppli | 340/259 |

*Primary Examiner*—Richard C. Queisser
*Assistant Examiner*—Charles Gorenstein
*Attorney, Agent, or Firm*—Kenyon & Kenyon, Reilly, Carr & Chapin

[57] ABSTRACT

A measuring head is used to measure a yarn characteristic while generating a continuous signal proportional to variations in the measured characteristic. The signal is multiplied by an identical second signal obtained either from a second measuring head located downstream of the first measuring head a distance corresponding to a predetermined periodic interval of yarn length (L) or by a time-delay of the first signal corresponding to the periodic interval (L). The multiplication of the signal deviations occurring at the periodic intervals, should such be present, produces a strong output signal indicative of the yarn irregularities. This output signal can be used to interrupt operation of the yarn processing machinery.

24 Claims, 7 Drawing Figures

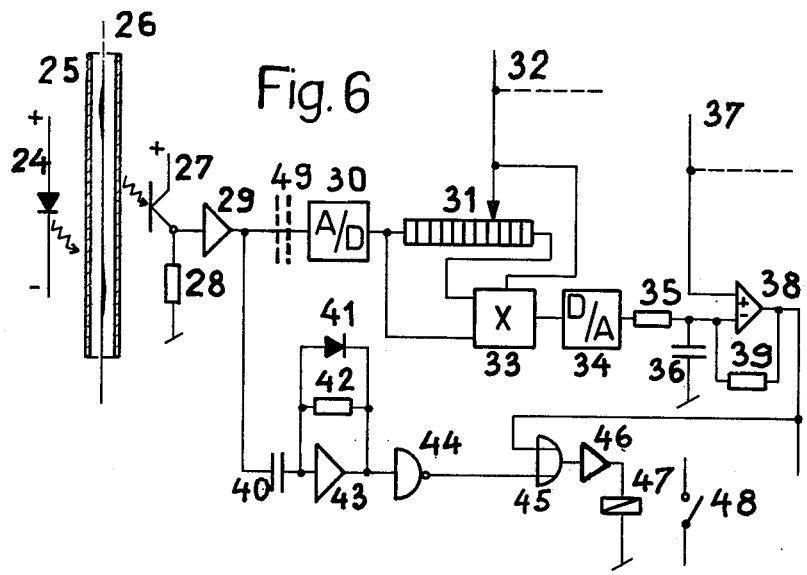
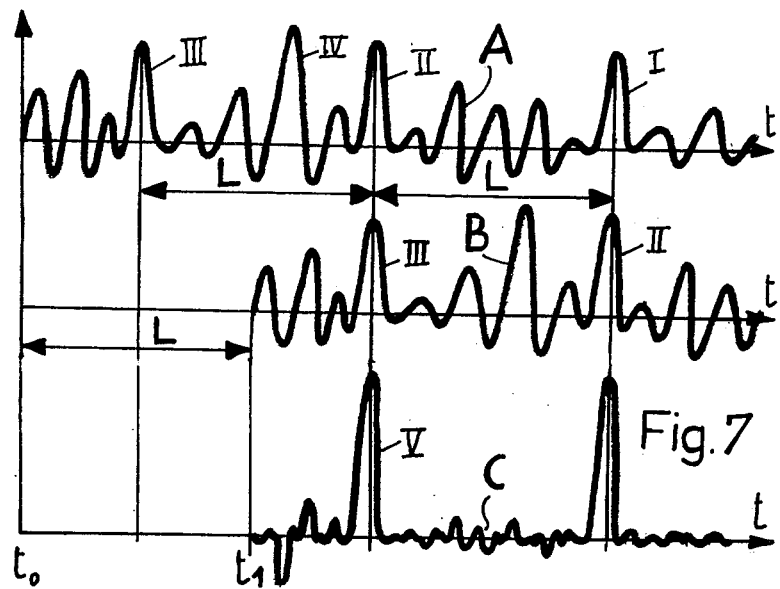

METHOD AND APPARATUS FOR DETECTING PERIODIC YARN IRREGULARITIES IN A YARN BETWEEN A YARN FORMING STAGE AND A YARN WINDING STAGE

This invention relates to a method and apparatus for detecting periodic yarn irregularities in a yarn between a yarn forming stage and a yarn winding stage.

As is known, yarns produced according to any yarn producing method are known to contain a smaller or larger number of yarn irregularities. In this context, the term "yarn irregularity" is understood to encompass places in the yarn which contain a number of fibers per cross-section which deviate from a determined and desired average value, i.e. places at which the fiber mass in the yarn deviates from the desired yarn count. In a yarn, thick and thin places are generally distinguished as places at which the fiber mass is either too large or too small. Also, the term "yarn irregularities" encompasses variations in the yarn cross-section area or in the yarn diameter. The occurrence of such yarn irregularities normally is caused by deficiencies of the spinning process, such as insufficient control of the draft attenuating the fiber mass, deficient blend intimacy of the fiber components and the like.

In the so-called Open-End spinning processes, a previously unknown cause of yarn irregularities has now been found. That is, it has been found that the presence of a particle of foreign matter, such as a cotton seed particle or a nep in the fiber collecting groove of a spinning rotor, causes variances in the resistance against twisting-in of the loose fibers which, in turn, cause yarn irregularities. These yarn irregularities show the particular characteristic that they are of pronounced periodicity, i.e. that the irregularities repeat themselves at regular intervals along the yarn body. The length of a period can correspond e.g. to the circumference of the groove of the spinning rotor which according to the diameter of the spinning rotor can range from about ten centimeters (10 cm) to fifty centimeters (50 cm). Such periodic yarn irregularities can also occur in other spinning methods such as ring spinning or in the so-called adhesive yarn formation methods. These irregularities are of primary importance in further yarn processing as they are responsible for the occurrence of so-called "moiré-effects" or diamond patterning in woven or knitted fabrics and the like.

A number of methods and devices are known in practice for preventing the occurrence of yarn irregularities, regardless whether they are of periodic character or not, between a yarn formation stage and a yarn winding stage of a yarn producing machine. For example, a spinning device is known for spinning yarns according to the open-end method (German patent application DOS No. 1,933,930) in which, among other elements, a yarn testing head is provided. This testing head is activated by yarn irregularities and acts as a trigger for opening the spinning rotor cover if the yarn quality is reduced or, if yarn irregularities are present and, thus, interrupts the further production of bad yarn.

The use of a yarn testing device on OE spinning machines is also known (German patent application DOS 2,242,151) for checking the yarn before winding the yarn by an electronic yarn fault detector and for cleaning the yarn by knotting out such yarn faults.

Although these known methods and devices allows the uncontrolled production of yarns containing irregularities to be avoided, these methods and devices do not permit a distinction between relatively harmless non-periodic yarn irregularities and the much more dangerous periodic yarn irregularities, the yarn mass deviation of which is possibly smaller. Thus, the occurrence of the moiré-effect or diamond patterning is not effectively prevented in spite of the considerable complexity of the devices.

A scanning and registering device for the yarn diameter has also been known, for example as described in U.S. Pat. No. 2,641,960 wherein the variations in yarn diameter can be measured, registered and analyzed. In this case, the periodic character of the diameter variation can be detected. Generally, the periodic character of the yarn cross-section can be detected by frequency filtering of the measuring signal using well determined, preselectable frequencies. A disadvantage of this device, however, resides in a requirement for filters with very steep selectivity lines. As a result, the center frequency must correspond exactly to a value proportional to the linear yarn speed in order to obtain a sufficient distance from the noise level.

As described in German patent application DOS No. 2,409,882, another known OE spinning method measures the yarn cross-section between the delivery of the yarn from the rotor and the cross-wound yarn package and transforms the measurement into an electrical signal. This signal is then analyzed for particularities which occur in periodic, excessively large thickness or diameter variations. A discriminator is activated if such particularities occur in the signal as a result of the disturbances mentioned above. However, this method does not take care of the periodic yarn irregularities, which are of the same order of magnitude as the normal yarn irregularities, as the detector used cannot discern them from the normal yarn irregularities. Thus, complete elimination of the moire or diamond patterning danger is not possible.

Other devices are also known which can detect the presence of variations in the yarn diameter which are of a determined periodicity length and which exceed a minimum value of variation of the yarn diameter. These devices function according to the very simple principle of counting the number of thick places in the yarn passing through. If this number equals the length of yarn divided by the preselected and suspected periodicity length, the presence of a periodic defect is considered as proven. This, however, is actually not the case in reality. These known devices also imply, just as the devices mentioned above, that the irregularities present in the yarn and to be detected distinctly exceed the noise level. The functional principle of such devices thus, is not reliable and is unsatisfactory.

Further measuring and analysing devices are also known, such as a yarn evenness tester and spectrograph made by the Zellweger Uster Company, which permit testing and analyzing of all geometrical or respectively gravimetrical properties of a yarn body. Due to the fact that the electrical signal generated as a function of, e.g. the yarn mass, is subject to a frequency analysis, it is possible to detect the presence of periodic yarn defects, the periodicity length of which is unknown, and to determine their periodicity length, even if they are caused by a periodic yarn defect of the same order of magnitude as the normal (non-periodic) yarn defects. Such known testing devices, which are ideally suited as such, require a complete frequency analysis of the measuring signal to be performed. As a result, these devices require use of a very complex and expensive electronic device and, thus, are feasible only as laboratory testing equipment but not as devices for continuous control of the performance e.g. of all yarn production points of a modern spinning machine equipped with a plurality of production units.

Accordingly, it is an object of the invention to provide a method which is capable of detecting the periodic character of yarn irregularities in a yarn passing from the point of yarn formation to a yarn winding point of a yarn producing machine even if these defects are of the same order of magnitude as normal non-periodic yarn irregularities.

It is another object of the invention to provide a simple technique for detecting periodic yarn irregularities in a yarn during production.

It is another object of the invention to provide a simple and economically feasible apparatus for detecting periodic yarn irregularities without performing a frequency analysis of a measuring signal.

It is another object of the invention to detect the presence of yarn irregularities of a predictable periodicity length in a yarn while the yarn is being produced, or at an early point in production and to prevent further irregularities immediately.

Briefly, the invention provides a method and apparatus for detecting periodic yarn irregularities which occur at predetermined intervals of length in a yarn passing between a yarn forming stage and a yarn winding stage of a yarn producing machine.

The method comprises the steps of continuously measuring a predetermined characteristic of the yarn at a first station during movement of the yarn from the forming stage to the winding stage and generating a first continuous electrical signal proportional to variations in the measured characteristic. In addition, the method includes the steps of generating a second signal identical to the first signal after a time lag corresponding to a multiple (one or more) of the periodic interval of yarn length and of continuously multiplying the first signal with the second signal to detect periodic yarn irregularities in the yarn.

The apparatus includes at least one measuring head positioned between the yarn forming stage and the yarn winding stage to continuously measure the yarn characteristic and to generate the first continuous signal as well as a control means for receiving the first signal. This control means has a multiplicator for multiplying the first signal with the second signal which lags the first signal by an amount equal to a multiple of the periodic interval of yarn length.

The second signal may be generated by storing the first signal in a signal store upstream of the multiplicator for a time corresponding to the periodic interval and then by transmitting the stored signal to the multiplicator.

Alternatively, the second signal can be generated by a second measuring head upstream of the multiplicator. In this case, the second measuring head is spaced from the first measuring head by a distance corresponding to the periodic interval of yarn length. This distance may be variable so as to adjust to other determined periodic intervals.

Where the yarn forming station employs an open-end spinning machine with a spinning rotor, the periodic interval of yarn length can correspond to a multiple of the circumference of a fiber collecting groove in the rotor.

These and other objects and advantages of the invention will become more apparent from the following detailed description and appended claims taken in conjunction with the accompanying drawings in which:

FIG. 6 illustrates an electrical circuit diagram according to the invention; and FIG. 7 diagrammatically illustrates the function of a method according to the invention based on a simplified indication.

Figure 1:
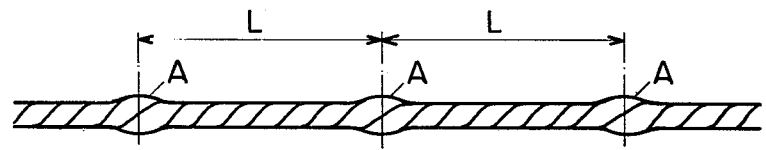
FIG. 1 illustrates a schematic view of a piece of yarn containing yarn irregularities of periodic character in the form of thick places.
Figure 2:
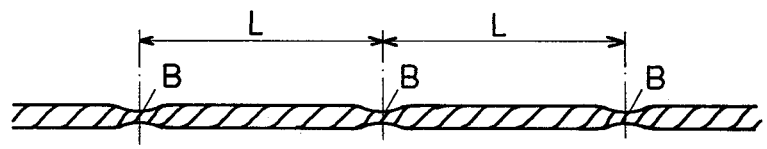
FIG. 2 illustrates a schematic view of a piece of yarn containing yarn irregularities of periodic character in the form of thin places.

Referring to FIG. 1, a yarn may contain periodically occurring enlargements of the fiber mass, i.e. so-called thick places A, or as shown in FIG. 2, may contain periodically occurring reductions of the fiber mass, i.e. so-called thin places B. The distance between two periodically successive yarn irregularities is designated L in both figures. This distance L can vary within certain limits.

Figure 3:
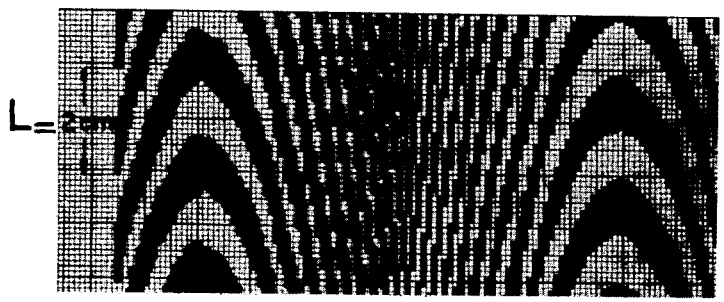
FIG. 3 illustrates a schematic view of the moire-effect in a textile fabric caused by periodic yarn irregularities.

The moiré-effect caused in a woven fabric by the presence of periodic yarn irregularities in the yarn, the periodicity length of which in the example shown in FIG. 3 is $L = 2$ centimeters (cm), renders the fabric entirely unusable. This can be proven in principle for any periodicity length L and in woven as well as in knitted fabrics.

Figure 4:
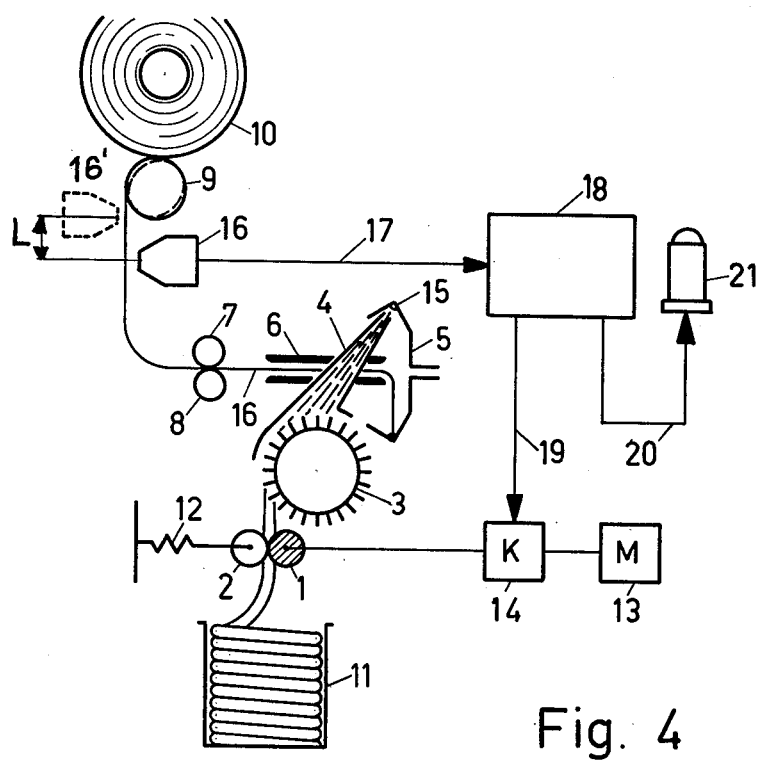
FIG. 4 illustrates a schematic view of an apparatus of the invention applied to an OE-rotor spinning machine.

Referring to FIG. 4, an open-end spinning unit, a larger number of which is always provided in an OE-rotor spinning machine for producing yarn, substantially consists of fiber supplying elements 1, 2, an opening roll 3, a fiber feed duct 4, a yarn forming stage in the form of a spinning rotor 5 with a fiber collecting groove 15, a yarn take-off tube 6, yarn delivery rolls 7, 8 and a yarn winding stage formed by various rolls 9, 10.

The fiber material is supplied in sliver form by the fiber supplying elements 1, 2 from a can 11. The fiber supplying elements consist e.g. of a driven fluted roll 1 and of a top roll 2 which is pressed against the fluted roll 1 by a spring 12. The fluted roll 1 is driven by a motor 13 which normally drives all fluted rolls 1 of one side of an OE-rotor spinning machine. In order to stop the fluted roll 1 of each spinning unit individually and independently of the motor 13, an electromagnetically controlled clutch 14 is incorporated between the motor 13 and fluted roll 1. Thus, the fiber supply to the spinning rotor 5 can be interrupted if needed, whereupon the yarn formation is interrupted immediately.

The function of the individual elements of the spinning unit mentioned above is known and, thus, no further explanation is needed in this context. In a spinning unit of this type, periodic yarn irregularities can occur. These irregularities are mainly caused by variable local conditions in the fiber collecting groove 15, for example due to the presence of contaminants in the groove 15. Such periodic irregularities, in this case, normally are of a predictable periodicity length, which corresponds to the circumference length of the fiber collecting groove 15 and causes particularly detrimental moiré-effects.

In order to detect such periodic yarn irregularities at an early time so as to permit cleaning out of any contaminants in the groove 15, a detection apparatus is positioned in the path of the yarn passing between the yarn forming stage, i.e. the rotor 5 and the yarn winding stage, i.e. the rolls 9, 10. This detection apparatus includes a measuring head 16 which is arranged between the spinning rotor 5, and the yarn winding rolls 9, 10 and which detects the variations of the yarn cross-section or of the yarn diameter or of the yarn mass. The measuring head 16 could also be arranged between the spinning rotor 5 and the yarn delivery rolls 7, 8. In particular, the measuring head 16 can be built into the yarn take-off tube 6, which arrangement presents certain structural advantages.

The measuring head 16 continuously measures the selected yarn characteristic of the passing yarn and generates a continuous electrical signal proportional to the variations of the measured characteristic. This signal is transmitted via a line 17 to a control means 18 of the apparatus.

The control means 18 analyzes and processes the received signal, as explained in more detail in the following.

If the control means 18 is triggered, an output signal is transmitted which activates the desired control function, by which, via a circuit 19, the clutch 14 is deactivated in such manner that the rolls 1, 2 are stopped and, thus, the fiber supply to the spinning unit is interrupted. A signal lamp 21 is also activated via a parallel circuit 20. Thus, the further production of faulty yarn, i.e. of yarn containing periodic irregularities is interrupted immediately at the spinning unit and this stage is signalled to the operator. The operator now can take care of the disturbed spinning conditions of the spinning unit, e.g. by cleaning the fiber collecting groove 15, and can restart the normal yarn production. This operation of re-establishing of impecable spinning conditions at each spinning unit could, of course, be effected partially or completely automatically.

In order to measure the yarn diameter or the yarn cross-section, use may be made of measuring heads which operate on an optical basis. In order to measure yarn mass, use of measuring heads which function capacitively are more suitable.

A system which is particularly suitable for application on an open-end rotor spinning machine is based on the principle of measuring the variations of the yarn mass by measuring the yarn tension.

As known, the following well approximated relation is established:

$$P = \frac{t \cdot \omega^2 \cdot R^2}{2} \cdot e^{\mu \frac{\pi}{2}}$$

where
P = yarn tension
ω = angular velocity of the spinning rotor
R = radius of the rotor
μ = coefficient of friction
t = specific yarn mass For a given machine (wherein R and μ are constant) and at constant rotor speed, the relation is thus:
P = K(t) where K is a constant.

Thus, it is sufficient to measure the variations of the yarn tension in order to obtain an indication of the yarn mass. The measuring head which measures the yarn tension in this arrangement is to be arranged between the spinning rotor 5 and the yarn delivery rolls 7, 8, as only in this section of the yarn path do the mass variations generate yarn tension variations.

The measuring head 16 and the control means 18 need not necessarily be arranged separately as shown in FIG. 4, but can be combined in one single unit.

Figure 5:
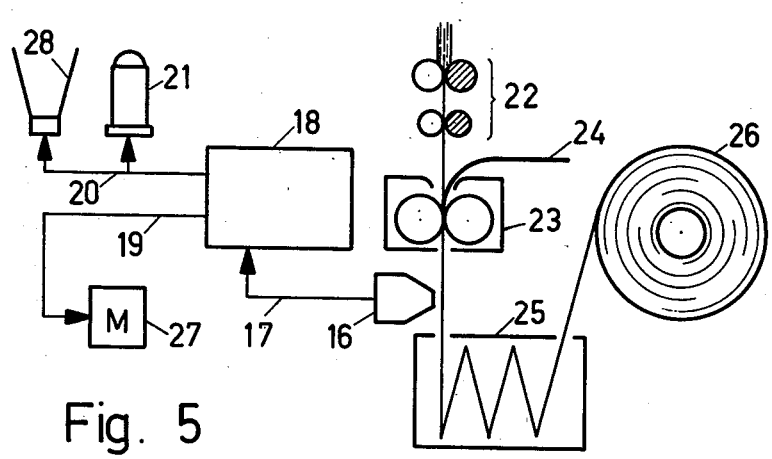
FIG. 5 illustrates a schematic view of an apparatus of the invention applied to a spinning machine producing adhesively bonded yarns.

Referring to FIG. 5, the detection method and apparatus can also be used on a yarn producing machine for the production of twistless, adhesively bonded yarns. As shown, the machine substantially consists of a drafting system 22, a liquid impregnation head 23 with an impregnating liquid supply duct 24, a drying unit 25 and a winding stage 26. The fiber material is drafted in the drafting system 22 to the required fineness, is impregnated in the impregnation head 23 with a suitable liquid, is dried in the dryer 25 and finally is wound onto a yarn take-up bobbin of the winding stage 26. A motor 27 drives all elements of the machine which are interconnected rigidly by, e.g. transmitting elements.

The measuring head 16 is arranged between the impregnation head 23, which is the stage of actual yarn formation, and the dryer 25 and functions according to the same principle described with reference to the example shown in FIG. 4. The only difference is that here, in case of the detection of a periodic yarn irregularity, the motor 27, i.e. the whole machine is stopped via the circuit 19 and that, via the circuit 20, not only the signal lamp 21 but also an acoustic horn 28 are activated.

The method and the apparatus for implementing the method can be principle be applied to any yarn producing machine. Most feasible, however, is the application on fast spinning machines, such as the spinning machines mentioned as examples with reference to FIGS. 4 and 5, where the dangers of occurrence of periodic yarn irregularities are most pronounced.

A feasible and sensible application of the invention can also be imagined on ring spinning machines, particularly if an increase in productivity per spindle can be achieved by suitable measures.

Referring to FIG. 6, the detection apparatus is provided with electronic control device shown with a simplified electric circuit in order to effect the required operation. This circuit comprises the elements described with references to FIGS. 4 and 5, i.e. a measuring head 16, control means 18 and circuit 17.

The electric circuit functions according to the principle, known in electronic measuring technology, of digital correlation measurement and shows the characteristic that the measuring head measuring periodic yarn irregularities is also to be used as a yarn breakage detector controlling the presence of the yarn.

The electronic control device consists of the following elements:
24 light emitting diode
25 glass tube
26 yarn to be tested
27 photo transistor
28 load resistor
29 amplifier
30 analog-digital transducer
31 shifting register
32 impulses from the spinning point, the impulse frequency of which is proportional to the yarn delivery speed
33 multiplicator The time-shifted signal and the direct signal are multiplied. The function orders, i.e. the order to shift the signal in the register by one step, and the order for the multiplication are given by the impulse 32.

34 digital-analog transducer
35/36 RC-member for establishing a mean value
38 amplifier as triggering value switch, in the circuit switched with a resistor 39
39 resistor
37 triggering voltage tension for the switch 38, preferably combined for a plurality of spinning units (central setting of the activation susceptibility of the measuring apparatus)
40 condenser for separating dc voltage
41 diode
42 resistor
43 amplifier
41-43 amplifier combined with simultaneous rectification
44 signal inversion stage (Not)
45 or-stage (OR)
46 output amplifier
47 relay
48 contactor switch for transmitting a signal for further processing (signal lamp, acoustic horn, deactivation of a clutch, etc.)
49 condenser The elements 30 – 33 and 45 – 48 are used for controlling the yarn on the occurrence of periodic yarn irregularities. The elements 40 – 48 form a yarn end breakage control.

The apparatus according to FIG. 6 functions as follows:

The measuring head (24 through 29), in the form of an optically functioning system with a light emitting diode 24 and a photo transistor 27, transmits an analog signal corresponding to the mass of the yarn 26 to be tested passing through the glass tube 25. This signal is transmitted and digitalized in the analog-digital transducer 30. The digitalized signal is shifted further in the shift register 31 which acts as a store to perform a storage function. After the lapse of a determined preselectable time lag, which corresponds to the periodicity length to be tested of the suspected periodic yarn irregularities and which can be preset via the number of registering points and the impulses 32 coming from the spinning point, the signal is transmitted to the multiplicator 33. The multiplicator then multiplys the signal with the momentaneous output signal of the analog-digital transducer 30. The output signal of the multiplicator 33 is transformed again in the digital-analog transducer 34 into an analog signal of which the RC member 35/36 determines the mean value. The transformations of the signal from analog-to-digital and then from digital-to-analog are not indispensable.

If a periodic yarn irregularity is present in the yarn, the periodicity length of which corresponds to the periodicity length tested, two signals of the same magnitude and of the same sense or direction are multiplied in the multiplicator 33 due to the time coincidence of the first signals stored in the shift register 31 and of the momentaneous signal. As a result, the output signal of the multiplicator 33 is strong and unmistakable for the detection of the periodicity of the yarn irregularities. The mean value of this signal is formed in the RC-member 35/36. If the voltage in the condenser 36 of the RC-member 35/36 now exceeds the triggering voltage 37 preset in the trigger value switch 38, this switch 38 transmits a signal, which is transmitted to the or-stage 45. The or-stage 45, in turn, activates the output amplifier 46 in such manner that, via the relay 47 and the contactor switch 48, a signal for activating the desired operations (lighting the signal lamp 21, activation of a clutch 14 (FIG. 4), de-activating a motor 27 (FIG. 5) etc.) is performed. If needed, the activation of the output amplifier 46 can be performed only after a minimum and presettable number of signals has been transmitted by the trigger value switch 38. The circuit arrangements needed for achieving this performance are known as such to any specialist trained in the field. Accordingly, the arrangement is not described in detail nor shown in the circuit diagram of FIG. 6.

The input of the or-stage 45 in this example can also be supplied via a secondary circuit in order to control end breakages. To this end, the measuring apparatus according to FIG. 6 is provided with the elements 40 through 43 for the yarn end breakage control. This secondary circuit consists of a condenser for separating the dc voltage 40, a diode 41, a resistor 42 and an amplifier 43. The circuit controls whether a variable portion is present at all times in the signal of the phototransistor 27, i.e. whether the yarn 26 in the glass tube 25 is moving. If a yarn 26 is absent or if a piece of yarn is stopped in the glass tube 25, a variable portion in the signal transmitted by the photo-transistor 27 is missing. This variable portion can be generated only by the movement of the yarn which always contains small mass deviations.

In case this variable portion is missing, a positive voltage prevails at the output of the signal inversion stage 44. This positive voltage is then transmitted via the or-stage 45. The or-stage 45 again, as in the case of the output of a correlation voltage mentioned above, activates the output amplifier 46 and, via the relay 47, the contactor switch 48. The contactor switch 48 then activates the start of the desired actions at the spinning unit.

As an alternative, a condenser 49, as indicated with broken lines in FIG. 6, can be used to adapt the mean signal value corresponding to the average yarn thickness. Thus, the measuring susceptibility of the measuring apparatus is increased and deviations of the measuring signal caused by thin places are also taken into account.

As shown with broken lines in FIG. 6, the periodicity length to be tested can be preset by means of the impulses 32 and the susceptibility of the measuring point can be preset by means of the triggering value voltage 37, preferably centrally for all spinning units of a whole spinning machine.

As an alternative to the correlation measurement described above with reference to FIG. 6, instead of using a store 31 to effect the shifting of the two signals to be multiplied two identical measuring heads can be spaced at a certain mutual distance corresponding to the expected periodicity length of the yarn irregularities or to a multiple thereof and used to test the yarn. The second measuring head 16' is indicated with broken lines in FIG. 4.

Obviously, the measuring apparatus shown in FIG. 6 does not depend on the use of an optical measuring head shown as an example as other systems suitable for detecting yarn irregularities can be used.

Also, instead of using a shift register 31 as a store, use may be made of a delay line circuit in which a transformation into a digital signal can be eliminated. In such a delay line circuit, the signal is also transmitted at a speed corresponding to the yarn speed. In this case, instead of the digital multiplicator 33, an analog multiplicator is used.

In FIG. 7, the functional principle of the method is visualized in more detail. The curve A schematically indicates the diagram of the electrical measuring signal transmitted by the elements 24 to 29 constituting the measuring head according to FIG. 6 as a function of time. The signal amplitude which is proportional to the characteristic of the measured yarn is plotted over time. The curve B is identical to the curve A but is shifted to the right over a time lag or delay $t_1 - t_0$, which corresponds to the time lag required for the production of a piece of yarn of a length corresponding to the predetermined periodicity length L.

The curve A and the identical, time-shifted curve B contain a periodic irregularity of the periodicity length L, i.e. at length intervals L deviations of the same sense or direction I, II, III, etc. are present. These deviations are of the same order of magnitude as the normal random deviations in the curves A and B respectively. The deviation IV is even somewhat larger than the aforementioned deviations I through III. In accordance with the above described method, the curve values of the curves A and B are multiplied. The result of this multiplication is shown in curve C, which is shown schematically. The curve C shows that the multiplication of two large deviations II of the curve A and III of the curve B result in a very pronounced deviation V in curve C, whereas the multiplication of the random deviations located between two periodic irregularities result in small deviations only in the curve C. Due to the random distribution of the deviations, they cancel themselves out to a large extent in the multiplication process. The curve B represents the signal stored in the shifting register 31 of FIG. 6, whereas the curve A represents the momentaneous measuring signal transmitted by the measuring head. As the curves A, B and C show, an unmistakable indication of the periodic deviations of the measuring signal shown in curve A and in the time-shiftd curve B is effected in the curve C.

The term "yarn characteristic" is understood in the context of the present invention to define any yarn characteristic which causes a moiré-effect in a textile fabric should the characteristic have a periodic variation. As an example of such yarn characteristics are the yarn diameter, the yarn cross-section area and the yarn mass.

The invention thus provides a method and apparatus which allows the possibility of completely liberating the production of yarns of the danger of producing defective yarns containing periodic yarn irregularities, particularly where the periodic yarn irregularities are of the same order of magnitude as normal non-periodic yarn defects. This can be achieved by using simple and inexpensive electrical circuits due to the fact that no frequency analysis of a measuring signal is required. Thus, the danger of producing textile fabrics containing moiré-effects is entirely excluded.

The apparatus, as shown in the example described with reference to FIG. 6, can be combined very easily with a yarn feeler for detecting end breakages which, in many cases, is provided at each spinning unit of a spinning machine. The circuits shown and/or described, which can be mass produced as each spinning machine usually contains a large number of spinning units, can be made at modest financial expense in such a manner that the economic feasibility of the use of a yarn measuring apparatus of this type is practical.

A further advantage is that the apparatus can be built into existing machines without difficulties.

What is claimed is:

1. A method of detecting periodic yarn irregularities occuring at predetermined intervals of length in a yarn passing between a yarn forming stage and a yarn winding stage of a yarn producing machine, said method comprising the steps of continuously measuring a predetermined characteristic of the yarn at a first station during movement of the yarn from the forming stage to the winding stage and generating a first continuous electrical signal proportional to variations in the measured characteristic;

generating a second signal identical to said first signal after a time lag corresponding to a multiple of the periodic interval of yarn length; and continuously multiplying said first signal with said second signal to detect periodic yarn irregularities in the yarn.

2. A method as set forth in claim 1 which further includes the step of storing said first signal during said time-lag to form said second signal.

3. A method as set forth in claim 1 wherein the yarn is measured at a second station downstream of said first station to generate said second signal.

4. A method as set forth in claim 1 which further comprises the step of forming the yarn in an open-end spinning machine at the yarn forming stage.

5. A method as set forth in claim 4 wherein the open-end spinning machine has a spinning rotor and said interval of length is a multiple of the circumference of a fiber collecting groove of the rotor.

6. A method as set forth in claim 1 wherein said interval of length is in the range of from two centimeters to one hundred centimeters.

7. A method as set forth in claim 1 wherein said interval of length is in the range of from 5 centimeters to 50 centimeters.

8. A method as set forth in claim 1 wherein said step of multiplying said signals produces a strong output signal in response to the presence of periodic yarn irregularities in the yarn.

9. A method as set forth in claim 8 wherein said step of multiplying produces said strong output signal only after multiplication of a certain number of deviations of the same magnitude and sense in said first and second signals.

10. A method as set forth in claim 8 which further comprises the step of interrupting the yarn production in response to said strong output signal.

11. A method as set forth in claim 8 which further comprises the step of producing at least one of an optical and an acoustical signal in response to said strong output signal.

12. A method as set forth in claim 1 wherein said first signal is an analog signal.

13. A method as set forth in claim 12 wherein said first signal is converted to a digital signal before multiplying with said second signal.

14. An apparatus for detecting periodic yarn irregularities occurring at predetermined intervals of length in a yarn passing between a yarn forming stage and a yarn winding stage of a yarn producing machine, said apparatus comprising at least one measuring head for positioning between the forming stage and the winding stage to continuously measure a predetermined characteristic of a yarn passing thereby and to generate a first continuous electrical signal proportional to variations in the measured characteristic; and a control means for receiving said first signal, said control means having a multiplicator for multiplying said first signal with a second momentaneous signal identical to said first signal and lagging said first signal by an amount equal to a multiple of the periodic interval of yarn length.

15. An apparatus as set forth in claim 14 wherein said control means includes a signal store upstream of said multiplicator for storing said second signal.

16. An apparatus as set forth in claim 15 wherein said store is a shifting register.

17. An apparatus as set forth in claim 14 wherein said control means includes an analog-to-digital transducer upstream of said multiplicator for converting said first signal from an analog signal to a digital signal.

18. An apparatus as set forth in claim 14 which further comprises a second measuring head for continuously measuring the yarn characteristic to generate said second signal, said second measuring head being disposed downstream of said one measuring head a distance equal to a multiple of said periodic interval of yarn length.

19. An apparatus as set forth in claim 18 wherein said second measuring head is adjustably movable relative to said one measuring head.

20. An apparatus as set forth in claim 14 wherein said control means has means for adjusting said amount of lag.

21. An apparatus as set forth in claim 14 wherein the yarn forming stage is an open-end spinning machine with a spinning rotor and said interval is a multiple of the circumference of a fiber collecting groove in said rotor.

22. An apparatus as set forth in claim 21 wherein said open-end spinning machine has a yarn take-off tube and said measuring head is built into said tube.

23. An apparatus as set forth in claim 21 wherein said measuring head detects variations of the spinning tension of the yarn as said yarn characteristic.

24. An apparatus as set forth in claim 14 wherein said measuring head detects the presence of the yarn and generates a signal in response thereto.

* * * * *

UNITED STATES PATENT AND TRADEMARK OFFICE
CERTIFICATE OF CORRECTION

PATENT NO. : 4,058,962

DATED : November 22, 1977

INVENTOR(S) : Gelli Spescha et al

It is certified that error appears in the above-identified patent and that said Letters Patent are hereby corrected as shown below:

Column 2, line 37, change "moire" to --moiré--

Column 10, line 48, after "certain" insert --minimum--

Signed and Sealed this

Twenty-first Day of November 1978

[SEAL]

Attest:

RUTH C. MASON
Attesting Officer

DONALD W. BANNER
Commissioner of Patents and Trademarks